United States Patent [19]

Miyake et al.

[11] Patent Number: 5,885,969
[45] Date of Patent: Mar. 23, 1999

[54] ENZYME-TREATED HESPERIDIN, PROCESS FOR PRODUCING THE SAME AND METHOD OF USING ENZYME-TREATED HESPERIDIN

[75] Inventors: Toshio Miyake, Okayama; Takashi Yumoto, Ichihara, both of Japan

[73] Assignee: Kabushiki Kaisha Hayashibara Seibutsu Kagaku Kenkyujo, Japan

[21] Appl. No.: 881,056

[22] Filed: Jun. 24, 1997

[30] Foreign Application Priority Data

Jun. 26, 1996 [JP] Japan ................................. 8-166464
Apr. 22, 1997 [JP] Japan ................................. 9-104272

[51] Int. Cl.$^6$ ................................................. A61K 31/70
[52] U.S. Cl. ................................................. 514/27
[58] Field of Search ................................. 514/27

[56] References Cited

U.S. PATENT DOCUMENTS

| | | | |
|---|---|---|---|
| 3,583,894 | 6/1971 | Horowitz et al. | 195/31 |
| 4,332,825 | 6/1982 | Miyawaki et al. | 426/330.5 |
| 5,077,206 | 12/1991 | Cheetham et al. | 435/99 |
| 5,641,659 | 6/1997 | Meiwes et al. | 435/105 |
| 5,652,124 | 7/1997 | Hijiya et al. | 435/78 |

FOREIGN PATENT DOCUMENTS 0402049  12/1990  European Pat. Off. .

OTHER PUBLICATIONS

Database WPI Section Ch, Week 9622, Derwent Publications Ltd., London, Great Britain: (1996) AN 96–216143, XP002065322 & Japanese Patent Laid Open No. JP 08 080 177 Abstract, Sep. 12, 1992, 1 page, English language.

Japanese Patent Abstract No. 3–7593, Jan. 14, 1991, 2 pages, (English language), 1 page (Japanese language).

Japanese Patent Abstract No. 8080177, Mar. 26, 1996, 1 page, (English language, 1 page (Japanese language).

Primary Examiner—Raymond Henley, III
Attorney, Agent, or Firm—Webb Ziesenheim Bruening Logsdon Orkin & Hanson, P.C.

[57] ABSTRACT

An enzyme-treated hesperidin, comprising alpha-glucosyl hesperidin, hesperidin and beta-monoglucosyl hesperetin, wherein the content of hesperidin is 0.1 part or less by weight; and that of beta-monoglucosyl hesperetin, 0.1 to 0.5 part by weight, on the basis of 1 part by weight of alpha-glucosyl hesperidin. The present invention also provides a process to produce enzyme-treated hesperidin, which comprises subjecting a solution containing alpha-glucosyl hesperidin and intact hesperidin to alpha-L-rhamnosidase to convert the intact hesperidin into beta-monoglucosyl hesperetin. The enzyme-treated hesperidin, which is excellent in water solubility and is free from crystal precipitation (clouding) even if stored for a prolonged period of time, can be produced from a material containing alpha-glucosylhesperidin and hesperidin by conducting the above simple treatment of material. The present invention further provides a method of using the enzyme-treated hesperidin. The enzyme-treated hesperidin can be used in the prevention of clouding of a canned tangerine and prevention of fading of natural coloring matter.

10 Claims, No Drawings

ENZYME-TREATED HESPERIDIN, PROCESS FOR PRODUCING THE SAME AND METHOD OF USING ENZYME-TREATED HESPERIDIN

BACKGROUND OF THE INVENTION

1. Field of the Invention

The present invention relates to an enzyme-treated hesperidin with a superior water solubility, as well as to its production and uses.

2. Description of Prior art

Hesperidin is the name of a compound where, as seen in the formula [I], rutinose or L-rhamnosyl-(alpha-6)-glucose is bound via beta-linkage to the hydroxyl group at 7-position in hesperetin or 5,7,3'-trihydroxy-4'-methoxyflavanone.

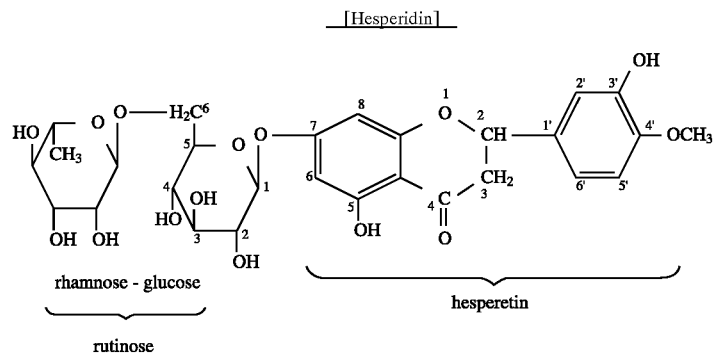

Hesperidin, which is contained in unripe pericarps of citruses, is used in medicines and cosmetics as a source of vitamin P. Vitamin P exhibits a variety of physiological activities such as those of strengthening the capillary blood vessel, preventing bleeding and regulating blood pressure. Hesperidin is soluble in aqueous alkaline solution but substantially insoluble in water and acids: Fifty liters of water dissolves only about 1 g hesperidin (about 0.002 v/v %) at ambient temperature. For example, even when a small amount of hesperidin is contained, in the syrup of canned products, the syrup may become turbid and impair their commercial value.

A variety of methods have been proposed which may prevent turbidity in syrups due to the presence of hesperidin.

For example, Japanese Patent Kokai No. 7,593/91 discloses a process to produce an enzyme-treated hesperidin with an elevated water solubility, where a saccharide-transferring enzyme, in particular, an enzyme possessing alpha-glucosyltransferase activity is allowed to act on hesperidin in the presence of a partial starch hydrolyzate as alpha-glucosyl saccharide compound to form alpha-glucosyl hesperidin as represented by the formula [II].

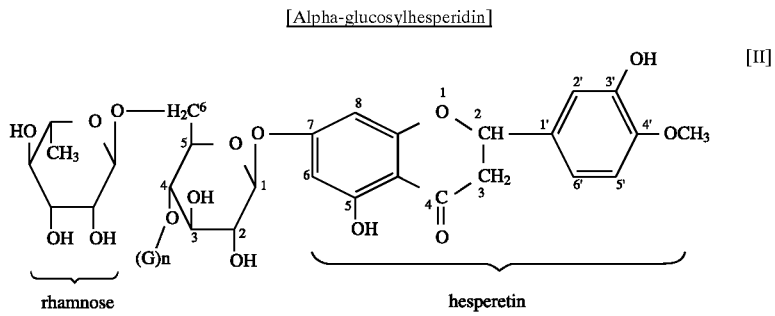

Alpha-glucosyl hesperidin is, as seen in the formula [II], either a single compound where n (1 to 20) units of glucose (G) are sequentially bound via 1,4-linkage to the glucose at the 4-position in hesperidin as represented by the formula [I], or a mixture of alpha-glucosyl hesperidins which differ from each other in the number of the glucose units.

In the above mentioned enzymatic reaction, 40 to 80% hesperidin in material liquid is converted into alpha-glucosyl hesperidin during the enzyme treatment, while 20 to 60% hesperidin remains intact. Although intact hesperidin exhibits a relatively high solubility in aqueous solution when alpha-glucosyl hesperidin coexists, an elevated ratio of intact hesperidin to alpha-glucosyl hesperidin results in the insolubilization and precipitation of hesperidin within a short time period.

One may contemplate another method which may prevent the precipitation of intact hesperidin, where glue materials such as carboxymethyl cellulose are added to solutions with hesperidin to elevate their viscosity. Such method is, however, generally unacceptable because the addition of glue material may reduce customer interest, as well as because the use of glue material is prohibited in products to be exported.

There is available still another method which may retard the precipitation of intact hesperidin, where intact hesperidin is precipitated and then removed by separation using, for example, filtration, thus decreasing the ratio of intact hesperidin to alpha-glucosyl hesperidin.

This method, however, does not provide complete solutions because the intact hesperidin still causes precipitation after a lapse of prolonged time period.

There is available still another method, where fractions of alpha-glucosyl hesperidin are isolated from an aqueous solution containing both alpha-glucosyl hesperidin and intact hesperidin by means, for example, of chromatographic separation, prior to its use. This method is, however, unacceptable from an economical viewpoint because it may result in increased cost.

To solve these problems, the present inventors have the found that when alpha-glucosyl hesperidin and intact hesperidin in solution are subjected to alpha-L-rhamnosidase (E.C.3.2.1.40), the former alpha-glucosyl hesperidin undergoes no changes and substantially remains intact, while the latter hesperidin is hydrolyzed into rhamnose and monoglucosyl hesperetin as represented by the formula [III]. This reaction yields an enzyme-treated hesperidin with a very superior water solubility which does not cause tubidity even when allowed to stand over a prolonged time period. The present invention is based on these findings.

The method, in which, in order to elevate the water solubility of hesperidin, alpha-L-rhamnosidase is allowed to act thereon to convert hesperidin into beta-monoglucosyl hesperetin, has been practiced on an industrial scale to prevent turbidity in the syrup of canned tangerines.

Prior Art, however, does not disclose the method of the present invention, where hesperidinase as an enzyme possessing alpha-L-rhamnosidase activity is allowed to act on a solution containing both alpha-glucosyl hesperidin and intact hesperidin so that the rhamnose moiety in the former alpha-glucosyl hesperidin is left intact, while that in the latter hesperidin is specifically hydrolyzed to change hesperidin into beta-monoglucosyl hesperetin, thus elevating the water solubility of the solution.

Japanese Patent Kokai No.80,177/96 discloses a method to prevent the precipitation of hesperidin crystals, where a solubilized hesperidin is added to a solution with hesperidin. Said Japanese Patent Kokai describes that the solubilized hesperidin is a compound where 1 to 10 or more glucose moieties are sequentially bound via alpha-1,4-linkage to the 4-position of the glucose moiety in hesperidin. This reference also teaches that the solubilized hesperidin can be produced by subjecting hesperidin in the presence of cyclodextrin to a saccharide-transferring enzyme which may be CGTase or 1,4-alpha-D-glucan; 1,4-alpha-D-(1,4-glucano)-transferase (E.C.2.4.1.19), for example, that harvested from cultures of strain A2-5a of the genus Bacillus.

Said Japanese Patent Kokai, however, discloses only the technical idea that solubilized hesperidin is admixed with intact hesperidin to prevent the precipitation of hesperidin crystals in products with hesperidin. Further, such a method gives a mixture of alpha-glucosyl hesperidin and hesperidin where intact hesperidin remains intact. Thus, canned products prepared by this method have the disadvantage that their syrups gradually become turbid. For coping with this problem, in the embodiments in the Japanese Patent Kokai, fractions of alpha-monoglucosyl and alpha-diglucosyl hesperidins are isolated, prior to uses. One may, however, encounter technical difficulties if he or she attempts to isolate the fractions at low cost.

OBJECT OF THE INVENTION

The purpose of the present invention is to solve these problems in the prior art. Main objects of the present invention are to provide an enzyme-treated hesperidin, obtainable from a mixture of alpha-glucosyl hesperidin and hesperidin through a simple processing, which is superior in water solubility and causative of neither precipitation of crystals nor turbidity even when stored for a prolonged time period, as well as to provide its method of production and uses.

Another object of the invention is to provide an enzyme-treated hesperidin which is favorably-usable to prevent turbidity in canned tangerines.

Still another object of the invention is to provide an enzyme-treated hesperidin which is suitably usable as agent directed to prevent the fading of natural coloring agents.

SUMMARY OF THE INVENTION

The enzyme-treated hesperidin of the present invention is characterized in that it contains alpha-glucosyl hesperidin along with hesperidin and beta-monoglucosyl hesperetin, in particular, 0.1 or less part by weight of hesperidin and 0.1 to 0.5 parts by weight of beta-monogluosyl hesperetin, on the basis of 1 part by weight of alpha-glucosyl hesperidin.

The process to produce enzyme-treated hesperidin according to the present invention is characterized by allowing alpha-L-rhamnosidase to act on a solution containing both alpha-glucosyl hesperidin and hesperidin, thereby converting or changing the latter hesperidin into beta-monoglucosyl hesperetin.

As to solutions which contain alpha-glucosyl hesperidin and hesperidin to be treated according to the present invention, it is preferable to use those which are obtained by allowing a saccharide-transferring enzyme to act on a solution which contains hesperidin together with an alpha-glucosyl saccharide compound.

In the present invention, it is preferable to use hesperidinase as enzyme possessing alpha-L-rhamnosidase activity.

Further in the present invention, preferably, the enzyme-treated hesperidins thus obtained contain alpha-glucosyl hesperidin along with hesperidin and beta-monoglucosyl hesperetin, in particular, 0.1 or less part by weight of hesperidin and 0.1 to 0.5 parts by weight of beta-monoglucosyl hesperetin, on the basis of 1 part by weight of alpha-glucosyl hesperidin.

Still further in the present invention, an enzyme with alpha-L-rhamnosidase activity, in particular, hesperidinase, is allowed to act on a solution containing alpha-glucosyl hesperidin and hesperidin to convert the latter hesperidin into beta-monoglucosyl hesperetin. The former alpha-glucosyl hesperidin can be changed into alpha-monoglucosyl and alpha-diglucosyl hesperidins by subjecting it to glucoamylase (E.C.3.2.1.3) or beta-amylase (E.C.3.2.1.2) simultaneously or successively with the present enzyme.

By the practice of the process according to the invention, one can obtain with ease an enzyme-treated hesperidin in the form of a composition comprising alpha-glucosyl hesperidin and beta-monoglucosyl hesperetin, which is very superior in water solubility and not causative of turbidity or precipitation of crystals.

Further, one can obtain an enzyme-treated hesperidin possessing both elevated alpha-glucosyl hesperidin content and commercial value by applying the alpha-glucosyl hesperidin of the present invention in solution to a column of preactivated adsorptive resin such as HP-20 and XAD-7 to effect adsorption of glycoside fractions, washing with water and eluting them with aqueous alcohol.

The enzyme-treated hesperidin of the present invention is capable of preventing turbidity in canned tangerines when incorporated therein. The enzyme-treated hesperidin is also capable of preventing turbidity in citrus beverages when incorporated therein. Further, the enzyme-treated hesperidin is capable of preventing the fading of natural coloring agents when used in combination. Still further, the fading of natural coloring agents is much more effectively prevented by using such a coloring agent together with the enzyme-treated hesperidin and enzyme-treated rutin and/or L-ascorbic acid.

DETAILED DESCRIPTION OF THE INVENTION

The enzyme-treated hesperidin and its production and uses will be described in detail below.

The enzyme-treated hesperidin of the present invention contains alpha-glucosyl hesperidin along with hesperidin and beta-monoglucosyl hesperetin, in particular, 0.1 or less part by weight of hesperidin and 0.1 to 0.5 parts by weight of beta-monoglucosyl hesperetin, on the basis of 1 part by weight of alpha-glucosyl hesperidin.

To produce such an enzyme-treated hesperidin, a solution containing both alpha-glucosyl hesperidin and hesperidin, as represented by the formulae [I] and [II] respectively, is subjected to an enzyme possessing alpha-L-rhamnosidase activity, in particular, hesperidinase, to convert or change the latter hesperidin in the solution into beta-monoglucosyl hesperetin as represented by the formula [III].

[Beta-monoglucosylhesperidin]

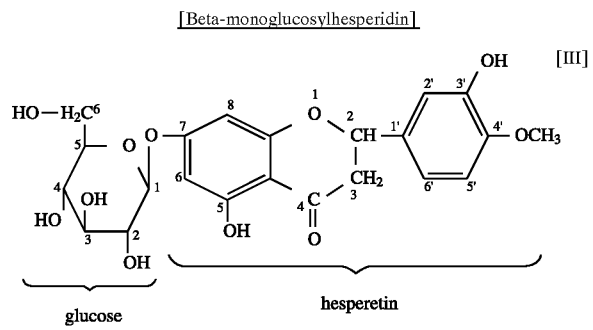

Solution containing alpha-glucosyl hesperidin and hesperidin

Any solutions are feasible in such enzymatic treatment regardless of their composition and concentration, as long as they contain both alpha-glucosyl hesperidin and hesperidin, where the concentration for alpha-glucosyl hesperidin in the solution to be treated is 0.1 to 30% by weight, preferably, 1 to 10% by weight; that for hesperidin, 0.02 to 15% by weight, preferably, 0.2 to 5% by weight; and wherein 1 to 200, preferably 1 to 25 parts by weight of hesperidin is contained on the basis of 100 parts by weight of alpha-glucosyl hesperidin.

Examples of such solution are as follows:

(1) a solution containing alpha-glucosyl hesperidin and intact hesperidin as described in Japanese Patent Kokai No. 7,593/91, which is obtained by allowing a saccharide-transferring enzyme as enzyme possessing alpha-glucosyl transferase activity to hesperidin in the presence of a partial starch hydrolysate as alpha-glucosyl saccharide compound, and (2) a solution with a decreased ratio of hesperidin to alpha-glucosyl hesperidin, which is obtained by precipitating hesperidin in the product obtained in the above, and separating and removing the hesperidin by means of filtration.

Enzyme possessing alpha-L-rhamnosidase activity

Any enzymes are feasible in the present invention as far as they possesses alpha-L-rhamnosidase activity; Examples of such enzyme include naringinase and, preferably, hesperidinase, both of which are commercially available from Tanabe Seiyaku Co., Ltd., Osaka, Japan.

Such enzyme is used, preferably, in an amount of 0.05 to 50 parts by weight, much more preferably, 1.5 to 15 parts by weight, on the basis of 100 parts by weight of hesperidin in a solution which contains alpha-glucosyl hesperidin and hesperidin.

To allow the enzyme to act on hesperidin in such solution, the solution is incubated, generally, at pH 3 to 7, preferably pH 3 to 4, and at 40° to 70° C., preferably 50° to 60° C. for 0.5 to 48 hours, preferably 6 to 24 hours.

When a solution containing alpha-glucosyl hesperidin and hesperidin is enzymatically treated under these conditions, the content of alpha-glucosyl hesperidin in the solution does not change before and after the treatment because alpha-glucosyl hesperidin is substantially insusceptible to alpha-L-rhamnosidase.

The enzyme-treated hesperidin thus obtained contains hesperidin in an amount of 0.1 or less part by weight, preferably, 0.02 or less part by weight, much more preferably, 0 to 0.01 part by weight along with beta-monoglucosyl hesperetin in an amount of 0.1 to 0.5 parts by weight, preferably, 0.15 to 0.4 parts by weight, much more preferably, 0.15 to 0.3 parts by weight, on the basis of 1 part by weight of alpha-glucosyl hesperidin.

Such enzyme-treated hesperidin is superior in water solubility: For example, it scarcely forms floc due to the precipitation of hesperidin even when prepared into 30% by weight aqueous solution and then allowed to stand at ambient temperature (25° C.) over 4 weeks while being observed macroscopically.

The alpha-glucosyl hesperidin thus obtained in the enzyme-treated hesperidin exhibits a variety of activities inherent to vitamin P when taken in the body because it is susceptible to enzymes in the body causing the release of hesperidin. In this case, combination with vitamin C attains a synergism in vitamin P activities including that of enhancing the resistance of the capillary blood vessels. Further, the enzyme-treated hesperidin may used to prevent the fading of natural coloring agents.

In this case, the enzyme-treated hesperidin is used in an amount of 0.001 to 0.2% by weight, preferably, 0.005 to 0.1% by weight, much more preferably, 0.01 to 0.05% by weight, based on the weight of products which are colored with natural coloring agents.

In greater detail, the use of hesperidin has been repeatedly attempted to prevent the fading of coloring agents, in particular, natural coloring agents which are uviosensitive to effect fading because hesperidin possesses a characteristic absorption spectrum in the ultraviolet region but no marked absorptions in visible region which render hesperidin almost colorless. These attempts have, however, been proved unsuccessful because hesperidin can not exhibit desired activities due to its very low solubility in water. Conventional enzyme-treated hesperidins, which were modified to elevate water solubility, have been unacceptable because precipitation and deposition of intact hesperidin may impair customers' interests.

By contrast, the enzyme-treated hesperidin of the present invention is extensively usable to prevent the fading of natural coloring agents because it is readily soluble in water and does not cause precipitation. In particular, it is effectively usable with coloring agents of carotenoid and flavonoid series such as paprika, beta-carotene, astaxanthin, grape skin extract and safflower yellow, as well as with other coloring agents including betanin, curcuma, gardenia yellow and ang-khak.

In this case, combination with enzyme-treated rutin and/ or either L-ascorbic acid or sodium L-ascorbate attains a synergism in the prevention of fading.

In the case of using the enzyme-treated hesperidin to prevent turbidity in canned tangerines, the amount of enzyme-treated hesperidin is set to 0.1 to 10 parts by weight, preferably, 0.1 to 2 parts by weight, much more preferably, 0.4 to 1 part by weight, on the basis of 1 part by weight of intact hesperidin which is present in the tangerine and syrup in canned tangerine.

Further, the present enzyme-treated hesperidin is usable to prevent turbidity in citrus beverages, for example, those of tangerine (*Citrus unshiu*), Valencia orange and grapefruit, which commonly contain hesperidin: In this use, the amount of enzyme-treated hesperidin is set to 0.1 to 10 parts by weight, preferably, 0.1 to 2 parts by weight, much more preferably, 0.4 to 1 part by weight, on the basis of 1 part by weight of intact hesperidin present in solutions.

Still further, the present enzyme-treated hesperidin is feasible as UV absorbent directed to use in cosmetics because it possesses a characteristic absorption in ultraviolet region but exhibits a very pale color.

By the practice of the present invention, one can obtain with great ease and at low cost an enzyme-treated hesperidin possessing a very superior water solubility by allowing alpha-L-rhamnosidase, in particular, hesperidinase as an enzyme possessing alpha-rhamnosidase activity, to act on a solution which contains alpha-glucosyl hesperidin and hesperidin.

The enzyme-treated hesperidin thus obtained causes no precipitation of hesperidin when allowed to stand over a prolonged time period because it scarcely contains hesperidin or, if it contains hesperidin, the content is very small, in particular, 0.1 or less part by weight against 1 part by weight of alpha-glucosyl hesperidin.

The enzyme-treated hesperidin of the present invention effectively prevents the fading of natural coloring agents.

The present enzyme-treated hesperidin effectively prevents turbidity in canned tangerines and citrus beverages when incorporated therein.

When taken in the body, alpha-glucosyl hesperidin as predominant component in the enzyme-treated hesperidin of the present invention is susceptible to enzymes causing the release of hesperidin which exhibits a variety of activities inherent to vitamin P because alpha-glucosyl hesperidin has been exposed to no enzymes other than alpha-L-rhamnosidase.

The enzyme-treated hesperidin of the present invention is extensively usable in usual food products including beverages and health foods, as well as in physiologically functional foods wherein one or more ingredients with physiological activities are incorporated to maintain and promote human health.

Further, the characteristic absorption in ultraviolet region renders the present enzyme-treated hesperidin usable as UV absorbent.

EXAMPLE

The present invention will be illustrated in greater detail with reference to the following Examples, which are, however, not intended to limit the scope of the present invention.

Example 1

Fifty grams of hesperidin was dissolved in 0.25N sodium hydroxide at ambient temperature (25° C.), and 150 g of dextrin (DE8) was added and dissolved in the resultant solution.

The resultant was adjusted to pH9.0 by the addition of 4N sulfuric acid, added with cyclodextrin glucanotransferase derived from the species *Bacillus stearothermophilus*, commercialized by Hayashibara Biochemical Laboratories, Inc., Okayama, Japan, in an amount of 15 units/g dextrin solid, adjusted to pH 7.0 by adding 4N sulfuric acid dropwise while heating to 60° C., heated to 68° C. and allowed to react for 40 hours.

After completion of the reaction, the reaction mixture was heated at 95° C. for 30 minutes to inactivate the enzyme and then filtered to obtain a solution of enzyme-treated hesperidin (referred to as "Solution A" hereinafter).

HPLC analysis of Solution A under the following conditions revealed that 72% by weight of hesperidin in the starting solution was converted into alpha-glucosyl hesperidin, while the remaining 28% by weight remained intact.

Analytical conditions of HPLC

The column used was C18; eluent, mixture of methanol/ water/acetic acid (volume ratio of 30:65:5); detection, 280 nm; temperature, 40° C.; and flow rate, 0.5 ml/minute.

(Absorption spectrum in ultraviolet region was determined at 200 to 400 nm using PDA detector.)

Solution A was adjusted to pH4.0 with 4N sulfuric acid, added with 2.0 g of "HESPERIDINASE #2", a hesperiginase product possessing alpha-L-rhamnosidase activity, commercialized by Tanabe Seiyaku Co., Ltd., Osaka, Japan, and allowed to react at 60° C. for 6 hours.

After completion of the reaction, the reaction mixture was heated at 95° C. for 30 minutes to inactivate the enzyme and then filtered to obtain a solution of enzyme-treated hesperidin (referred to as "Solution B" hereinafter).

HPLC analysis of Solution B under the above conditions revealed that the alpha-glucosyl hesperidin underwent no substantial change and remained intact in Solution B, while a major part (99% or more by weight) of intact hesperidin in Solution A was changed into beta-monoglucosyl hesperetin. Identification of hesperidin, beta-monoglucosyl hesperetin alpha-monoglucosyl hesperidin and alpha-glucosyl hesperidin Hesperidin, beta-monoglucosyl hesperetin, alpha-monoglucosyl hesperidin and alpha-glucosyl hesperidin were identified in the following manner.

1. Hesperidin

Identification was carried out using an authentic reagent of hesperidin, manufactured by Tokyo Kasei Kogyo Co., Ltd., Tokyo, Japan.

2. Beta-monoglucosyl hesperetin

The authentic reagent of hesperidin was first subjected to alpha-L-rhamnosidase, then analyzed with high-performance liquid chromatography (abbreviated hereinafter as "HPLC") under the above conditions. Thereafter, a single peak fraction (RT (retention time)=12.13) following a peak of hesperidin (RT=10.90) was collected, hydrolyzed and determined for glucose. Further, It was confirmed that the ultraviolet absorption spectrum of the fraction was in accordance with that of hesperidin, thus identifying the single peak fraction to be of beta-monoglucosyl hesperetin or hesperetin-7-glucoside.

3. Alpha-monoglucosyl hesperidin and alpha-glucosyl hesperidin

The reaction mixture from the authentic reagent of hesperidin was analyzed with HPLC under the above conditions. The ultraviolet absorption spectra of each peak fraction were checked for agreement with that of hesperidin. Further, the reaction mixture was subjected to glucoamylase and then analyzed with HPLC under the above conditions. As the result, each peak faction commonly gave a single peak (RT=10.34) preceding that of hesperidin (RT=10.90).

After collecting the fraction (RT=10.34), it was confirmed that it gave glucose and hesperidin when subjected to alpha-glucosidase (E.C.3.2.1.20). Thus, the peak (RT=10.34) was identified as alpha-monoglucosyl hesperidin, while this peak and a group of peaks with less RT was identified as alpha-glucosyl hesperidin.

Measurement of weight of hesperidin, beta-monoglucosyl hesperetin, alpha-monoglucosyl hesperidin and alpha-glucosyl hesperidin The weight of hesperidin, beta-monoglucosyl hesperetin, alpha-monoglucosyl hesperidin and alpha-glucosyl hesperidin were determined in the following manner.

1. Hesperidin

Specimens were analyzed with HPLC and weight was determined using an authentic reagent of hesperidin, manufactured by Tokyo Chemical Industry Co., Ltd., Tokyo, Japan.

2. Beta-monoglucosyl hesperetin

Specimens were analyzed with HPLC and weight was determined while estimating their molecular weight using the authentic reagent of hesperidin.

3. Alpha-monoglucosyl hesperidin

Specimens were analyzed with HPLC and weight was determined while estimating their molecular weight using the authentic reagent of hesperidin.

4. Alpha-glucosyl hesperidin fraction

One gram of the fraction was dissolved in 50 ml water, applied at SV1 to 100 ml of XAD-7 which had been activated in concentrated aqueous ethanol and sufficiently washed with water, after which elution was effected with 200 ml of 50% aqueous ethanol. The eluate was separated from ethanol, concentrated, dried and its weight was determined. When hesperidin and/or beta-monoglucosyl hesperetin was detected in the eluate on HPLC analysis, the weights determined according to the above items 1 and 2 were subtracted from that determined for the eluate.

Example 2

Solution A as alpha-glucosyl hesperidin solution, which had been separately prepared, was added with both 0.5 ml of "GLUCZYME NL4.2", a glucoamylase product (4,200 units/ml) commercialized by Amano Pharmaceutical Co., Ltd., Nagoya, Japan, and 2.0 g "HESPERIDINASE #2", a hesperidinase product commercialized by Tanabe Seiyaku Co., Ltd., Osaka, Japan, adjusted to pH4.0 with 4N sulfuric acid and allowed to react at 55° C. for 48 hours.

After completion of the reaction, the reaction mixture was heated at 90° C. for 30 minutes to inactivate the enzymes and then filtered to obtain a solution of enzyme-treated hesperidin (referred to as "Solution C" hereinafter).

HPLC analysis of Solution C under the conditions in Example 1 revealed that a major part of alpha-glucosyl hesperidin was changed into alpha-monoglucosyl hesperidin in Solution C, while a major part (99% or more) of intact hesperidin was turned into beta-monoglucosyl hesperetin.

Thereafter, Solution C was applied to a column of 1.5L "XAD-7", a porous adsorptive resin with a moderate polarity, which had been activated in concentrated aqueous ethanol, after which the column was washed with water 2-fold larger than the volume of the resin, followed by desorption of the adsorbed components using 3L of 60 (v/v) % aqueous ethanol.

The eluate was separated from ethanol and lyophilized to obtain 44.8 g of an enzyme-treated hesperidin (referred to as "Solid D" hereinafter).

Example 3

Solution A as a solution of enzyme-treated hesperidin (Solution A), which had been separately prepared, was added with 0.5 ml of "GLUCZYME NL4.2", adjusted to pH 5.0 with 4N sulfuric acid and allowed to react at 55° C. for 24 hours. After completion of the reaction, the reaction mixture was heated at 90° C. for 30 minutes to inactivate the enzyme and then filtered to obtain a solution of enzyme-treated hesperidin (referred to as "Solution E" hereinafter).

HPLC analysis of Solution E under the conditions described in Example 1 revealed that a major part of alpha-glucosyl hesperidin was changed into alpha-monoglucosyl hesperidin in Solution E, while intact hesperidin underwent no substantial change in Solution E.

Thereafter, as in Example 2, Solution E was applied to a column of 1.5L "XAD-7", a porous adsorptive resin with a moderate polarity, which had been activated in concentrated aqueous ethanol, after which the column was washed with water 2-fold larger than the volume of the resin, followed by desorption of the adsorbed components using 3L of 60 (v/v) % aqueous ethanol.

The eluate was separated from ethanol and then lyophilized to obtain 48.0 g of an enzyme-treated hesperidin (referred to as "Solid F" hereinafter).

Flocculation test

Solutions A and B as solutions of enzyme-treated hesperidin were separately added with water to give respective solid contents of 30% by weight, while Solids D and F were separately dissolved in pure water to give respective solid contents of 15% by weight, after which each solution was sterilized by heating, distributed in 200 ml aliquots in sterile glass vials and then allowed to stand for 4 weeks while checking for relationship between the number of standing days and the amount of floc formed during the standing.

TABLE 1

(Flocculation observation results)

| Sample | No. of days passed | | | | | |
|---|---|---|---|---|---|---|
| | 1 | 3 | 7 | 14 | 21 | 28 |
| enzyme-treated hesperidin (A) | − | + | ++ | +++ | +++ | +++ |
| enzyme-treated hesperidin (B) | − | − | − | − | − | − |

TABLE 1-continued (Flocculation observation results)

| | No. of days passed | | | | | |
|---|---|---|---|---|---|---|
| Sample | 1 | 3 | 7 | 14 | 21 | 28 |
| enzyme-treated hesperidin (D) | – | – | – | – | – | – |
| enzyme-treated hesperidin (F) | – | ++ | +++ | ++++ | ++++ | ++++ |

The criteria of evaluation were as follows: The symbol "–" was given when no floc was formed; "+", when trace amount of floc was formed; "++", when a small amount of floc was formed; "+++", when a large amount of floc was formed; and "++++", when a great amount of floc was formed.

The weight ratios for components in the enzyme-treated hesperidin specimens were as shown in Table 2.

TABLE 2

(Component weight ratios of enzyme-treated hesperidins)

| Sample | α-glucosyl-hesperidin | hesperidin | β-monoglucosyl-hesperetin |
|---|---|---|---|
| enzyme-treated hesperidin (A) | 1.0 | 0.21 | 0.0 |
| enzyme-treated hesperidin (B) | 1.0 | 0.01 | 0.15 |
| enzyme-treated hesperidin (D) | 1.0 | 0.01 | 0.24 |
| enzyme-treated hesperidin (F) | 1.0 | 0.21 | 0.0 |

Example 4

One and half grams of citric acid in citric acid monohydrate form, 0.13 g of sodium citrate in the form of trisodium citrate dihydrate and 200 g of granulated sucrose were dissolved in water to give a total amount of 1,000 g. The resultant solution was added with hesperidin which had been dissolved in alkaline water, in particular, 0.2N aqueous solidum hydroxide to 2.0% by weight, and adjusted to pH3.0 with 1N hydrochloric acid, thus obtaining a test solution with a hesperidin content of 0.05% by weight.

Two hundred gram aliquots of the test solution were added with 200 mg of Solid D in Example 2, which had been dissolved to 10% by weight, to provide "Test run 1" with 0.01% by weight of enzyme-treated hesperidin.

Similarly as above, "Test run 2" and "Test run 3" respectively were provided with 0.02% by weight and 0.04% by weight of enzyme-treated hesperidin.

Further provided was a run without enzyme-treated hesperidin as a control, as shown in Table 3.

Test runs 1 to 3 and control were allowed to stand at ambient temperature over 1 week while macroscopically checking them for turbidity.

The results were as shown in Table 3

TABLE 3

(Visual inspection of turbidity)

| | No. of days passed | |
|---|---|---|
| plots | 3 | 7 |
| plot 1 (enzyme-treated hesperidin 0.01 wt. %) | – | ± |
| plot 2 (enzyme-treated hesperidin 0.02 wt. %) | – | – |

TABLE 3-continued (Visual inspection of turbidity)

| | No. of days passed | |
|---|---|---|
| plots | 3 | 7 |
| plot 3 (enzyme-treated hesperidin 0.04 wt. %) | – | – |
| control plot | ++* | ++* |

*: a large amount of precipitate occurred.

Evaluation was made according to the following criteria:

The criteria of evaluation were as follows: the symbol "–" was given when no turbidity occurred; "±", when a trace turbity occurred; "+", when a small turbidity occurred; and "++", when a large or marked turbidity occurred.

Example 5

Solid D in Example 2 as enzyme-treated hesperidin was added to 0.05% by weight of gardenia yellow in citric acid buffer (pH3.3) to give a content of 0.02 or 0.04% by weight for enzyme-treated hesperidin, after which, as shown in Table 4, either or both of "alpha G Rutin PS", an enzyme-treated rutin consisting of 77.5% by weight of alpha-monoglucosyl rutin, 14.5% by weight of isoquercitrin, 5.2% by weight of saccharide and 2.8% by weight of water, commercialized by Toyo Sugar Refining Co., Ltd., Tokyo, Japan, and L-ascorbic acid were simultaneously added, sterilized by heating in closed vessels and then determined for remaining rate (%) of gardenia yellow on alternate days at a wave length of 442 nm using spectrometry while irradiating with a fluorescent lamp (7,000 lux).

The test conditions and results were as given in Tables 4 and 5 respectively.

There was provided as a control an additional run without addition as shown in Tables 4 and 5.

Further provided were "Test run 10" and "Test run 11" respectively with enzyme-treated rutin and L-ascorbic acid as shown in Tables 4 and 5.

TABLE 4-1

(Test condition/unit: wt. %)

| Additive | Test No. | | | | | | | |
|---|---|---|---|---|---|---|---|---|
| (wt. % in soln.) | 1 | 2 | 3 | 4 | 5 | 6 | 7 | 8 |
| enzyme-treated hesperidin | 0.02 | 0.02 | 0.02 | 0.02 | 0.04 | 0.04 | 0.04 | 0.04 |
| enzyme-treated rutin | 0 | 0.02 | 0 | 0.02 | 0 | 0.04 | 0 | 0.04 |
| L-ascorbic acid | 0 | 0 | 0.02 | 0.02 | 0 | 0 | 0.04 | 0.04 |

TABLE 4-2

(Test condition/unit: wt. %)

| Additive | Test No. | | |
|---|---|---|---|
| (wt. % in soln.) | 9 | 10 | 11 |
| enzyme-treated hesperidin | 0 | 0 | 0 |
| enzyme-treated rutin | 0 | 0.02 | 0 |
| L-ascorbic acid | 0 | 0 | 0.02 |

Note: test No. 9: blank (control plot).

TABLE 5-1

(Result/value indicates survival rate % of gardenia yellow coloring matter)

| No. of days passed | Test No. | | | | | | | |
|---|---|---|---|---|---|---|---|---|
| | 1 | 2 | 3 | 4 | 5 | 6 | 7 | 8 |
| 0 | 100 | 100 | 100 | 100 | 100 | 100 | 100 | 100 |
| 2 | 62 | 67 | 73 | 75 | 69 | 82 | 86 | 86 |
| 4 | 36 | 48 | 53 | 56 | 48 | 69 | 71 | 73 |

TABLE 5-2

(Result/value indicates survival rate % of gardenia yellow coloring matter)

| No. of days passed | Test No. | | |
|---|---|---|---|
| | 9 | 10 | 11 |
| 0 | 100 | 100 | 100 |
| 2 | 20 | 64 | 63 |
| 4 | 3 | 41 | 39 |

Note: Test No. 9: blank (control plot).

Each Test run commonly exhibited an improved remaining rate (%) for gardenia yellow as compared with that in control. Comparison of Test run 5 with Test run 1, where enzyme-treated hesperidin was used in different amounts but neither enzyme-treated rutin nor L-ascorbic acids was added, confirmed that the remaining rate was improved by 12% as determined on the forth day when the addition of enzyme-treated hesperidin in solution increased from 0.02 to 0.04% by weight.

A synergistic effect was confirmed when enzyme-treated hesperidin was used in combination with enzyme-treated rutin and/or L-ascorbic acid.

Example 6

Three hundred grams of a juice from tangerine (*Citrus unshiu*), 95 g of granulated sucrose, 0.12 g of citric acid in the form of citric acid monohydrate and 1.0 ml of flavoring agent were admixed in water to obtain 1,000 g citrus beverage (fruit juice based beverage). One hundred ml aliquots of the beverage were added with Solution A in Example 1 in an amount of 4 mg (0.004% by weight), 8 mg (0.008% by weight) or 12 mg (0.012% by weight) on dry solid basis, thus obtaining Test runs 1 to 3 respectively. Test runs 4 to 6 were provided similarly as above, except that, in place of Solution A, Solution B in Example 1 was used in an amount of 4 mg (0.004% by weight), 8 mg (0.008% by weight) or 12 mg (0.012% by weight). Further provided was a run without enzyme-treated hesperidin as a control. Each run was allowed to stand at an ambient temperature while macroscopically checking them for turbidity.

The results were as shown in Table 6.

TABLE 6

| | | Visual inspection results | | | | | |
|---|---|---|---|---|---|---|---|
| | Amt. of added | | No. of days passed | | | | |
| Test plot | enzyme-treated hesperidin | at start | 2 days | 1 week | 2 weeks | 3 weeks | 6 weeks | 10 weeks |
| 1 | 0.004 wt. % | − | − | ± | + | ++ | ++ | ++ |
| 2 | 0.008 wt. % | − | − | − | ± | + | ++ | ++ |
| 3 | 0.012 wt % | − | − | − | − | − | − | − |
| 4 | 0.004 wt. % | − | − | − | ± | ++ | ++ | ++ |
| 5 | 0.008 wt. % | − | − | − | − | − | ± | + |
| 6 | 0.012 wt. % | − | − | − | − | − | − | − |
| control plot | | − | + | ++ | +++ | +++ | +++ | +++ |

Turbidity:
−: clear,
±: slightly turbid,
+: turbid on low level,
++: turbid on low but increased level, and
+++: highly turbid (precipitation in large amount).

What is claimed is:

1. An enzyme-treated hesperidin, comprising alpha-glucosyl hesperidin, hesperidin and beta-monoglucosyl hesperetin,
   wherein the content of hesperidin is 0.1 part or less by weight; and that of beta-monoglucosyl hesperetin, 0.1 to 0.5 part by weight, on the basis of 1 part by weight of alpha-glucosyl hesperidin.

2. The enzyme-treated hesperidin of claim 1, which contains 0.15 to 0.4 parts by weight of beta-monoglucosyl hesperetin, on the basis of 1 part by weight of alpha-glucosyl hesperidin.

3. A process to produce enzyme-treated hesperidin, which comprises subjecting a solution containing alpha-glucosyl hesperidin and intact hesperidin to alpha-L-rhamnosidase to convert the intact hesperidin into beta-monoglucosyl hesperetin.

4. The process of claim 3, wherein said solution is obtainable by subjecting a solution containing hesperidin along with an alpha-glucosyl saccharide compound to a saccharide-transferring enzyme.

5. The process of claim 3, wherein said alpha-L-rhamnosidase is hesperidin use.

6. The process of claim 3, wherein said enzyme-treated hesperidin contains 0.1 or less part by weight of hesperidin and 0.1 to 0.5 parts by weight of beta-monoglucosyl hesperetin, on the basis of 1 part by weight of alpha-glucosyl hesperidin.

7. A method to prevent turbidity in canned tangerines, which comprises incorporating in canned tangerines an effective amount of the enzyme-treated hesperidin of claim 1.

8. A method to preventing turbidity in citrus beverages, which comprises incorporating in citrus beverages an effective amount of the enzyme-treated hesperidin of claim 1.

9. A method to preventing fading of natural coloring agents, which comprises allowing the enzyme-treated hesperidin of claim 1 to coexist with natural coloring agents.

10. The method of claim 9, wherein the enzyme-treated hesperidin is used in combination with enzyme-treated rutin and/or L-ascorbic acid.

* * * * *

UNITED STATES PATENT AND TRADEMARK OFFICE
CERTIFICATE OF CORRECTION

PATENT NO. : 5,885,969

DATED : March 23, 1999

INVENTOR(S) : Toshio Miyake and Takashi Yumoto

It is certified that error appears in the above-identified patent and that said Letters Patent is hereby corrected as shown below:

Column 1, in Cell [II], approx. line 40: "O ___ $H_2C^6$" delete --$^6$--.

Column 4, Line 26 "is favorably usable" should read --is useful--.

Column 6 Line 21 delete semicolon and insert period --.--.

Column 6 Line 61 "may used" should read --may be used--.

Column 7 Line 6 before "visible" insert --the--.

Column 7 Line 34 after "hesperidin" delete colon and insert period --.--.

Column 8 Lines 45-46 "hesperiginase" should read --hesperidinase--.

Column 9 Line 31 "The weight" should read --The weights--.

Column 10 after Line 57 and before Table 1, insert: --The results were as shown in Table 1.--.

Column 11 Table 2, column 4 heading: "hesperetin" should read --hesperidin--.

Column 11 Line 56 after "as shown in Table 3" insert period --.--.

UNITED STATES PATENT AND TRADEMARK OFFICE
CERTIFICATE OF CORRECTION

PATENT NO.   : 5,885,969
DATED        : March 23, 1999
INVENTOR(S)  : Toshio Miyake and Takashi Yumoto It is certified that error appears in the above-identified patent and that said Letters Patent is hereby corrected as shown below:

Column 15 Line 2 Claim 5 "hesperidin use" should read --hesperidinase--.

Signed and Sealed this

Sixteenth Day of November, 1999

Attest:

Q. TODD DICKINSON

*Attesting Officer*     Acting Commissioner of Patents and Trademarks